US00PP23594P2

(12) United States Plant Patent
Bruinen

(10) Patent No.: US PP23,594 P2
(45) Date of Patent: May 14, 2013

(54) ***ZAMIOCULCAS ZAMIIFOLIA* PLANT NAMED 'LUCKY'**

(50) Latin Name: *Zamioculcas zamiifolia*
Varietal Denomination: LUCKY

(75) Inventor: Edward Bruinen, Maasdijk (NL)

(73) Assignee: Edplant B.V., Maasdijk (NL)

( * ) Notice: Subject to any disclaimer, the term of this patent is extended or adjusted under 35 U.S.C. 154(b) by 0 days.

(21) Appl. No.: 13/374,454

(22) Filed: Dec. 28, 2011

(51) Int. Cl.
*A01H 5/00* (2006.01)

(52) U.S. Cl.
USPC ..... Plt./263.1

(58) Field of Classification Search ..... Plt./263.1
See application file for complete search history.

*Primary Examiner* — Annette Para
(74) *Attorney, Agent, or Firm* — Cassandra Bright

(57) ABSTRACT

A new and distinct *Zamioculcas zamiifolia* cultivar named 'LUCKY' is disclosed, characterized by rounded leaves and a short, compact plant habit. The new variety is a *Zamioculcas zamiifolia*, normally produced as an ornamental plant.

1 Drawing Sheet

Latin name of the genus and species: *Zamioculcas zamiifolia.*

Variety denomination: 'LUCKY'.

BACKGROUND OF THE INVENTION

The new *Zamioculcas zamiifolia* cultivar is a product of a chance discovery by the inventor, Edward Bruinen, in Maasdijk, The Netherlands. The inventor identified and selected the interesting mutation of *Zamioculcas zamiifolia* and proceeded to test its suitability for ornamental commercial applications.

The parent is an unpatented, unnamed variety of *Zamioculcas zamiifolia*. The new variety was discovered in September 2003, by the inventor as a naturally occurring whole plant mutation, in a commercial greenhouse in Maasdijk, The Netherlands.

Asexual reproduction of the new cultivar 'LUCKY' by vegetative cuttings was first performed at a commercial greenhouse in Maasdijk, The Netherlands in September 2007 and has shown that the unique features of this cultivar are stable and reproduced true to type in successive generations. Plants of the new variety have not been sold at the time of filing this application.

SUMMARY OF THE INVENTION

The cultivar 'LUCKY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LUCKY' These characteristics in combination distinguish 'LUCKY ' as a new and distinct *Zamioculcas zamiifolia* cultivar:

1. Unique round shaped foliage.
2. Short and compact plant habit.

Plants of the new cultivar 'LUCKY' are similar to plants of the parent, *Zamioculcas zamiifolia*. in most horticultural characteristics, however, plants of the new cultivar 'LUCKY' produce round leaves compared to the ovate leaves of the parent. The leaf apex of 'LUCKY' is rounded whereas the parent has an acuminate leaf apex. Additionally, the plant shape of 'LUCKY' is somewhat more compact than that of the parent.

COMMERCIAL COMPARISON

Plants of 'LUCKY' are best compared to the parent variety.

BRIEF DESCRIPTION OF THE PHOTOGRAPHS

The accompanying photograph in FIG. 1 illustrates in full color a typical plant of 'LUCKY' grown in a greenhouse, in a 17 cm pot. Age of the plant photographed is approximately 13 months from a rooted cutting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'LUCKY' plants grown in a greenhouse, in Maasdijk, The Netherlands. The growing temperature ranged from 20° C. during the day to 18° C. during the night. General light conditions are normal sunlight. Measurements and numerical values represent averages of typical plant types. Plants are approximately 13 months old from a rooted cutting.

Botanical classification: *Zamioculcas zamiifolia* 'LUCKY'.

PROPAGATION

Time to initiate roots: About 14-21 days at approximately 22° C.

Root description: Moderately free branched, thick, non-fibrous, non-fleshy, coloured grey-brown; 199B.

Time to produce rooted plantlet: Approximately 4-5 weeks at approximately 22° C.

PLANT

Growth habit: Upright, narrow inverted triangular.
Plant shape: Narrow inverted triangular.
Height: Approximately 34.6 cm to top of highest leaf.
Plant spread: Approximately 29.9 cm in a 17 cm pot.
Growth rate: Moderate.
Branching characteristics: Not branching, leaves grow directly from a basal clump.
Number of clumps: Average: 1.
Number of stems per clump: Average 6.
Number of leaves per plant: Approximately 66.
Age of plant described: Approximately 13 months.

FOLIAGE

Leaf:
*Arrangement*.—Leaves alternately paripinnate.
*Average length* (*excluding petiole*).—Approximately 19.5 cm (measured from lowest leaflet to top).
*Average width*.—Approximately 12.7 cm.
Leaflets:
*Shape of blade*.—Leaflets ovate to elliptic.
*Average length*.—Approximately 5.8 cm.
*Average width*.—Approximately 3.9 cm.
*Aspect*.—Flat to somewhat undulating along margin.
*Apex*.—Rounded.
*Base*.—Rounded.
*Margin*.—Entire.
*Texture of top surface*.—Smooth, very glossy.
*Texture of bottom surface*.—Smooth, very glossy (but slightly less than upper side).
*Color*.—Young foliage upper side: Near RHS Green 143A. Young foliage under side: Near RHS Yellow-Green 144A. Mature foliage upper side: Near RHS Green 141A. Mature foliage under side: Near RHS Green, 143A.
Venation:
*Type*.—Pinnate.
*Venation coloration upper side*.—Near RHS Green 143A.
*Venation coloration under side*.—Near RHS Yellow-Green 144A.
Rachis:
*Length*.—Approximately 24.7 cm.
*Width*.—At narrowest point: Approximately 0.3 cm. Above clump: Approximately 1.8 cm.
*Color*.—Near RHS Yellow-Green 147B.
*Strength*.—Very strong.
*Texture*.—Smooth, dull, glabrous.
Other structures: None present.

FLOWER

Typically non flowering: No flowers, no reproductive organs observed.

OTHER CHARACTERISTICS

Seed production: Not observed to date.
Disease resistance: Neither resistance nor susceptibility to diseases or pests has been observed in this variety.
Temperature tolerance: Low temperature tolerance to at least 5° C., high temperatures to at least 40° C.
Drought tolerance: Moderate tolerance for drought.

What is claimed is:

1. A new and distinct cultivar of *Zamioculcas zamiifolia* plant named 'LUCKY' as herein illustrated and described.

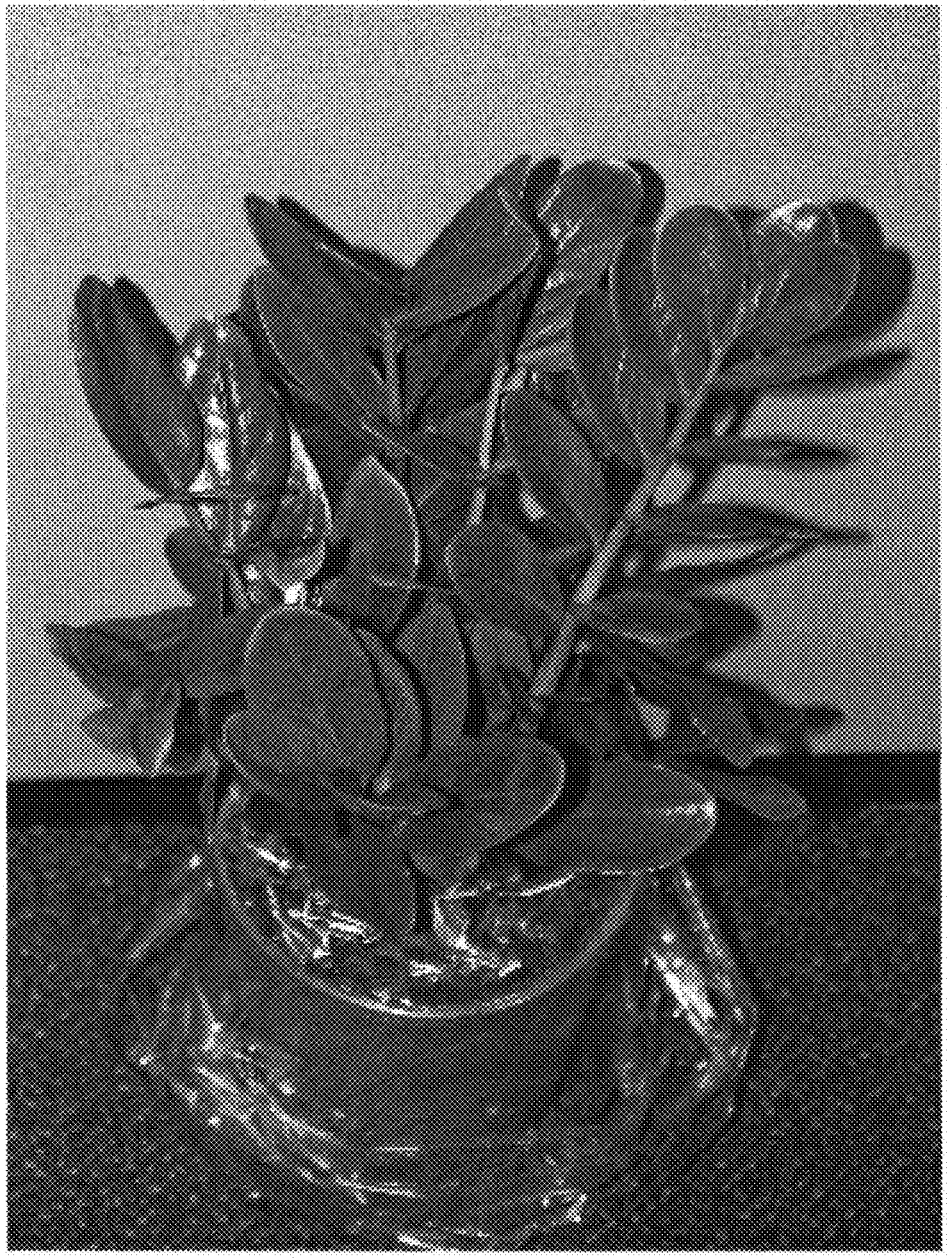

* * * * *